Figure 1A:
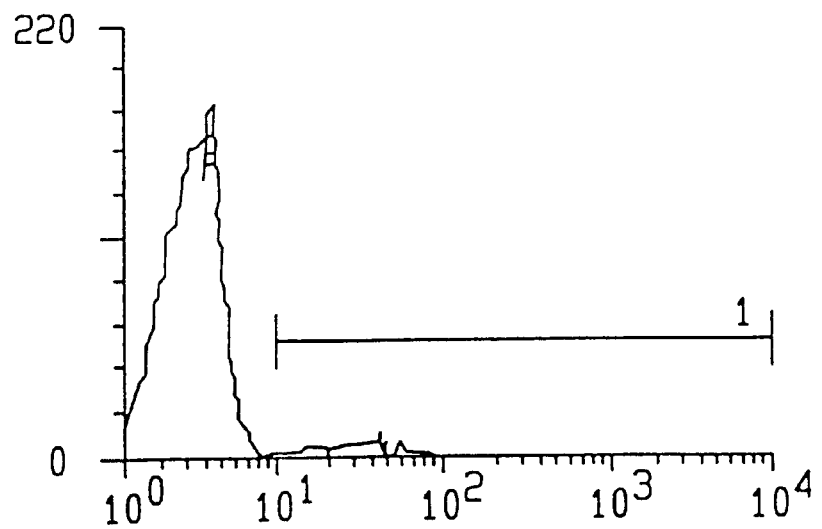

United States Patent [19]

Ildstad et al.

[11] Patent Number: 6,013,519

[45] Date of Patent: *Jan. 11, 2000

[54] MONOCLONAL ANTIBODIES TO ANTIGENS EXPRESSED BY HEMATOPOIETIC FACILITATORY CELLS

[75] Inventors: Suzanne T. Ildstad, Pittsburgh; Christina Kaufman, Munhall; Yolanda Colson, Pittsbugh, all of Pa.

[73] Assignee: University of Pittsburgh, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/914,300

[22] Filed: Aug. 18, 1997

Related U.S. Application Data

[63] Continuation of application No. 08/464,918, Jun. 5, 1995, abandoned, which is a continuation of application No. 08/177,501, Jan. 5, 1994, abandoned.

[51] Int. Cl.[7] ............................ C12N 5/12; C12N 5/20; C07K 16/28
[52] U.S. Cl. ...................... 435/343.1; 435/70.21; 435/452; 435/325; 435/326; 435/332; 435/343; 530/387.1; 530/388.1; 530/388.2; 530/388.7; 530/388.73
[58] Field of Search .......................... 530/387.1, 388.1, 530/388.73; 435/70.21, 326, 343.1

[56] References Cited

FOREIGN PATENT DOCUMENTS 451611  3/1991  European Pat. Off. .......... C12N 5/08

OTHER PUBLICATIONS

Idstad et al. Transplantation 41:372–376 (1986).
Sykes et al. J. Immunol. 143: 3503–3511(1989).
Kaufman et al. Blood 82(10 suppl 1):456A (1993).
Kaufman et al. J. Immunol. 150(8 Part 2): 321A (1993).
ATCC Catalog of Cellines and Hybridomis, 7th ED 1992 p. 434.
Daul Fundamental Immunol. Raven Press NY 1993 p. 242 Only.

Primary Examiner—Christina Y. Chan
Assistant Examiner—Phillip Gambel
Attorney, Agent, or Firm—Pennie & Edmonds LLP

[57] ABSTRACT

The present invention relates to monoclonal antibodies (MAb) to hematopoietic facilitatory cells (FC). In particular, it relates to MAb against antigens expressed by murine FC, methods of generating the antibodies, and methods of using the same. MAb directed to markers that are expressed specifically or at higher levels by FC than by most other bone marrow cells have a wide range of applications, including but not limited to, rapid isolation of FC, identification of FC in a donor cell preparation, and molecular cloning of the genes encoding the corresponding target antigens.

6 Claims, 3 Drawing Sheets

MONOCLONAL ANTIBODIES TO ANTIGENS EXPRESSED BY HEMATOPOIETIC FACILITATORY CELLS

This is a continuation of application Ser. No. 08/464,918, filed Jun. 5, 1995, (abandoned) which is a continuation of application Ser. No. 08/177,501, filed Jan. 5, 1994 (abandoned).

1. INTRODUCTION

The present invention relates to monoclonal antibodies (MAb) to hematopoietic facilitatory cells (FC). In particular, it relates to MAb against antigens expressed by murine FC, methods of generating the antibodies, and methods of using the same. MAb directed to markers that are expressed specifically or at higher levels by FC than by most other bone marrow cells have a wide range of applications, including but not limited to, rapid isolation of FC, identification of FC in a donor cell preparation, and molecular cloning of the genes encoding the corresponding target antigens.

2. BACKGROUND OF THE INVENTION

A major goal in solid organ transplantation is the engraftment of the donor organ without a graft rejection immune response generated by the recipient, while preserving the immunocompetence of the recipient against other foreign antigens. Typically, nonspecific immunosuppressive agents such as cyclosporine, methotrexate, steroids and FK506 are used to prevent host rejection responses. They must be administered on a daily basis and if stopped, graft rejection usually results. However, nonspecific immunosuppressive agents function by suppressing all aspects of the immune response, thereby greatly increasing a recipient's susceptibility to infections and diseases, including cancer.

Furthermore, despite the use of immunosuppressive agents, graft rejection still remains a major source of morbidity and mortality in human organ transplantation. Only 50% of heart transplants survive 5 years and 20% of kidney transplants survive 10 years. (See Powles, 1980, Lancet, p. 327; Ramsay, 1982, New Engl. J. Med., p. 392). Most human transplants fail within 10 years without permanent acceptance. It would therefore be a major advance if tolerance can be induced in the recipient.

The only known clinical condition in which complete systemic donor-specific transplantation tolerance occurs reliably and reproducibly is when chimerism is created through bone marrow transplantation. (See Qin et al., 1989, J. Exp. Med. 169:779; Sykes et al., 1988, Immunol. Today 9:23; Sharabi et al., 1989, J. Exp. Med. 169:493). This has been achieved in neonatal and adult animal models as well as in humans by total lymphoid irradiation of a recipient followed by bone marrow transplantation with donor cells. The widespread application of bone marrow transplantation to areas outside of malignancy has been limited by graft-versus-host disease (GVHD). The success rate of bone marrow transplantation is, in part, dependent on the ability to closely match the major histocompatibility complex (MHC) of the donor cells with that of the recipient cells. The MHC is a gene complex that encodes a large array of individually unique glycoproteins expressed on the surface of both donor and host cells that are the major targets of transplantation rejection immune responses. In the human, the MHC is referred to as HLA. When HLA identity is achieved by matching a patient with a family member such as a sibling, the probability of a successful outcome is relatively high, although GVHD is still not completely eliminated. The incidence and severity of GVHD are directly correlated with degree of genetic disparity. In fact, only one or two antigen mismatch is acceptable because GVHD is very severe in cases of greater disparities. When allogeneic bone marrow transplantation is performed between two MHC-mismatched individuals of the same species, common complications involve failure of engraftment, poor immunocompetence and a high incidence of GVHD.

GVHD is a potentially lethal complication in bone marrow transplantation, which occurs in about 35–50% of recipients of untreated HLA-identical marrow grafts (Martin et al., 1985, Blood 66:664) and up to 80% of recipients of HLA-mismatched marrow. Unfortunately, only 30% of patients generally have a suitably matched HLA-identical family member donor, and thus most patients are either excluded from being considered for bone marrow transplantation, or if they are transplanted must tolerate a high risk of GVHD. GVHD results from the ability of immunocompetent mature immune cells (mainly T cells, but some B cells and natural killer cells) in the donor graft to recognize host tissue antigens as foreign and invoke an adverse immunologic reaction. Although mixed allogeneic reconstitution, in which a mixture of donor and recipient marrow is transplanted, results in improved immunocompetence and increased resistance to GVHD, successful engraftment is still not consistently achieved and GVHD still often occurs.

Recent studies in bone marrow transplantation suggest that the major cause of GVHD are T-cells, as the removal of T cells from the donor cell preparation was associated with a reduction in the incidence of GVHD. (Vallera et al., 1989, Transplant, 47:751; Rayfield, 1984, Eur. J. Immunol., P. 308; Vallera, 1982, J. Immunol., 128:871; Martin and Korngold, 1978, J. Exp. Med., p 1687; Prentice, 1984, Lancet P. 472). After T-cells were implicated to be the predominant mediator of GVHD in animal models, aggressive protocols for T-cell depletion (TCD) of human donor bone marrow were instituted. Although the incidence of GVHD was decreased dramatically, TCD was accompanied by a significant increase in the failure of engraftment, indicating that T cells might also play a positive role in bone marrow engraftment. (Soderling, J. Immunol., 1985, 135:941; Vallera, 1982, Transplant. 33:243; Pierce, 1989, Transplant., p. 289). The increase in failure of engraftment in human recipients ranged from about 5–70% of total patients and was related to the degree of MHC disparity between the donor and recipient (Blazar, 1987, UCLA Symp., p. 382; Filipovich, 1987, Transplant., p. 62; Martin et al., 1985, Blood 66:664; Martin et al., 1988, Adv. Immunol. 40:379). Patients with failed engraftment usually die even if a second bone marrow transplant is performed. Consequently, most transplant institutions in the United States have abandoned TCD of donor bone marrow and, thus, must tolerate a high level of GVHD which leads to significant morbidity and mortality. Thus, the application of bone marrow transplantation as a form of treatment is limited only to settings where the potential of GVHD is clearly outweighed by the potential benefit. It was therefore anticipated that the administration of purified bone marrow stem cells would optimize engraftment and avoid GVHD. However, recent studies have shown that purified bone marrow stem cells only engraft in genetically identical, but not in genetically disparate recipients.

The implication that T cells might participate in both harmful GVHD reactions and helpful engraftment facilitation was an enigma that existed for a long time in the scientific community. Investigators began to search for the possible existence of a bone marrow component which could facilitate bone marrow engraftment but was removed during TCD. Identification and purification of this facilitating component would potentially allow the design of transplant protocols to selectively prevent GVHD, while preserving the cells that can enhance engraftment.

Although most investigators speculated that the facilitating component was a hematopoietic cell distinct from the hematopoietic stem cells, such a component had never been identified or characterized until recently. In fact, all evidence pointed towards the involvement of some form of T cells. It was recently discovered that a cell population referred to as FC facilitates engraftment of hematopoietic stem cells in a recipient without producing GVHD, and this cell expresses several markers shared by other leukocytes. The identification of specific markers expressed by FC would greatly assist the rapid isolation of this cell type.

3. SUMMARY OF THE INVENTION

The present invention relates to MAb directed to antigens expressed by murine FC, methods of generating the antibodies and methods of using the same to isolate FC.

The invention is based, in part, on the Applicants' discovery that FC play a critical role in promoting the ability of donor hematopoietic stem cells to engraft in a lethally-irradiated allogeneic or xenogeneic recipient. Although murine FC are morphologically distinct from all other known cell types and they have been shown to express Thy-1, CD2, CD3, CD5, CD8, CD45, CD45R and MHC class II (in the low to intermediate range as compared to B cells and dendritic cells), these markers individually do not readily distinguish the FC from other bone marrow cells. Therefore, the isolation and enrichment of FC currently employ a cumbersome and time-consuming multiple step procedure involving positive and negative selection. In order to develop a method for rapid identification of FC in a cell mixture and their subsequent isolation therefrom, MAb may be produced to antigens specifically or more selectively expressed by FC than by other cells, assuming such antigens exist.

The generation of MAb requires the use of FC as immunogens, but since FC are present in natural tissue sources at low quantities (approximately 0.05%), it is practically difficult to obtain a high yield of an enriched population of FC for use in immunization. While whole bone marrow preparation with little or no enrichment for FC may be used as immunogens, it is unlikely that MAb can be raised to FC markers since other bone marrow cells are present in much higher numbers and express other highly immunogenic antigens which may dominate the antibody responses to the FC-associated molecules.

In an effort to generate MAb to FC, it is recognized that FC may share certain cell surface antigens with brain tissue as shown by the ability of rabbit-anti-mouse brain (RAMB) antiserum to reduce the level of donor bone marrow cell engraftment, presumably due to a depletion of FC. Thus, brain tissue is prepared and used to immunize animals. Cell fusion is performed using spleen cells from immunized animals and the resultant hybridomas are first screened for the secretion of antibodies in their supernatants. Thereafter, the MAb are further screened for their ability to deplete FC activity in vivo, as manifested by mixed allogeneic chimerism in recipients following reconstitution with donor bone marrow cells treated with the antibodies. MAb exhibiting such activities in this screening procedure are selected for further characterization.

The invention is described by way of examples in which mouse brain tissue is prepared and used to immunize rats. After several immunizations, the rats are sacrificed and their spleen cells fused with mouse myeloma cells. The resultant hybridomas are first screened for their secretion of rat antibodies of IgG or IgM isotypes. The positive hybridomas are further tested by reacting their supernatants with mouse donor (H-$2^k$) bone marrow cells prior to their co-administration with TCD H-$2^b$ donor bone marrow into H-$2^b$ recipients. In this model, untreated allogeneic donor bone marrow cells give rise to fully (100%) allogeneic chimeras, whereas RAMB or anti-Thy-1 antibody-treated donor cells produce low levels of mixed allogeneic chimerism, if any, in recipients, presumably due to the diminution of FC in the donor cell preparation. Three MAb, designated R7.6.2, R340.3.1 and R373.6.3 are capable of depleting FC, producing mixed allogeneic chimeras. A wide variety of uses for MAb to antigens expressed by FC are encompassed by the invention described herein, including but not limited to, the identification of FC in a donor cell preparation, the isolation and enrichment of FC from a cell mixture, and the molecular cloning of the corresponding target antigens.

4. BRIEF DESCRIPTION OF THE DRAWINGS

Figure 1B:
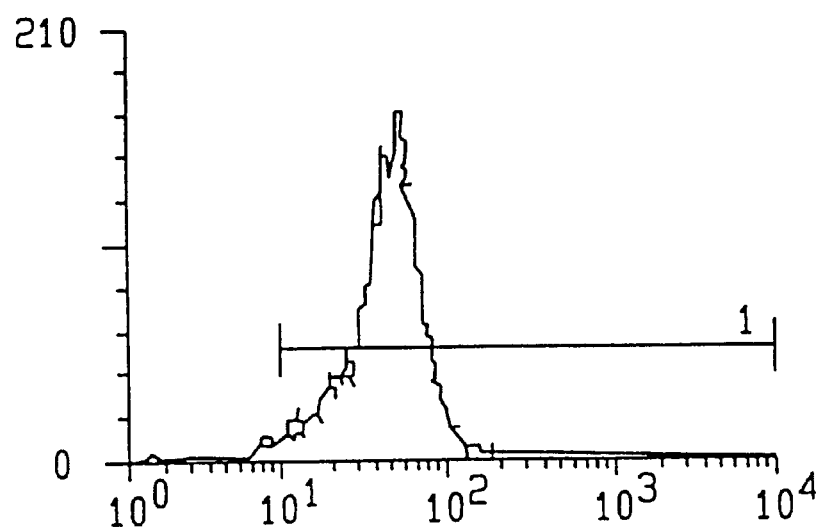

FIGS. 1A and 1B Untreated donor bone marrow cells produce fully allogeneic chimeras. Only allogeneic cells (H-$2^k$) are detected.

Figure 2A:
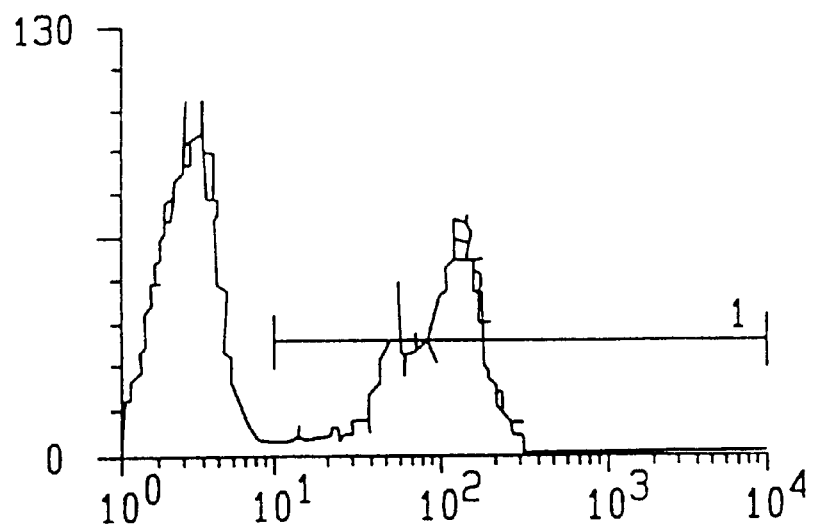
Figure 2B:
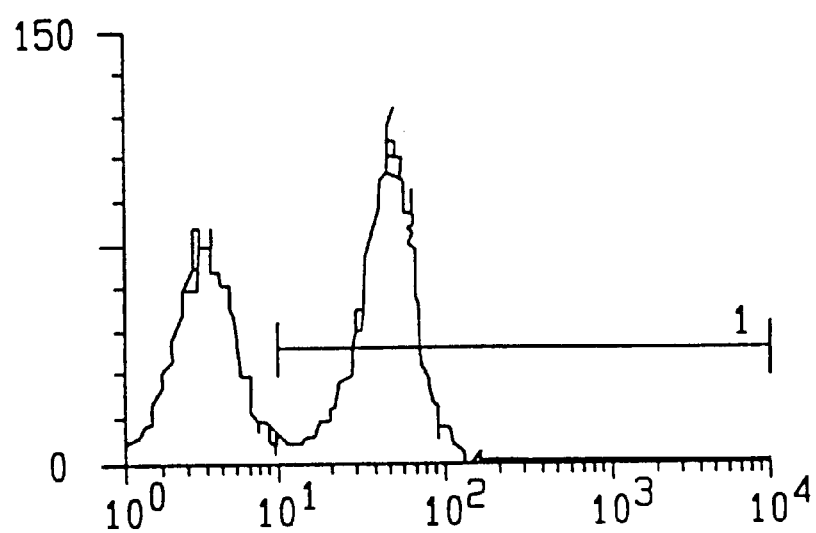

FIGS. 2A and 2B RAMB-treated donor bone marrow cells produce mixed allogeneic chimeras. Both syngeneic and allogeneic cells are detected.

Figure 3A:
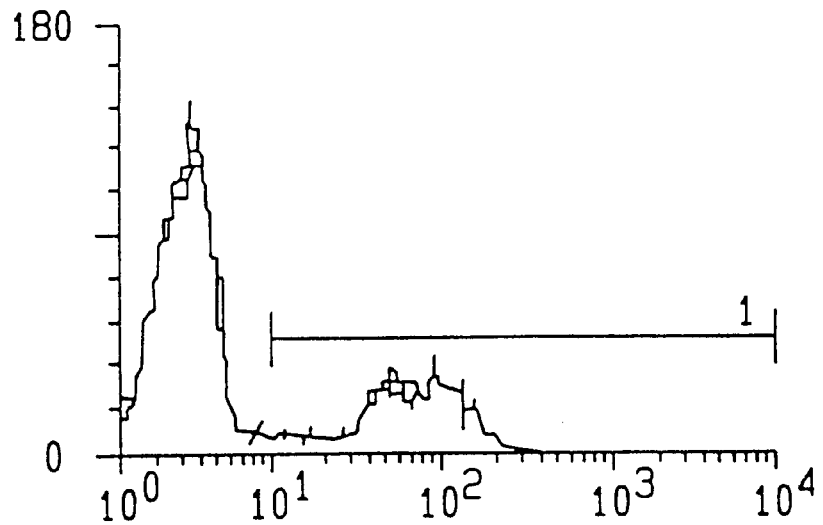
Figure 3B:
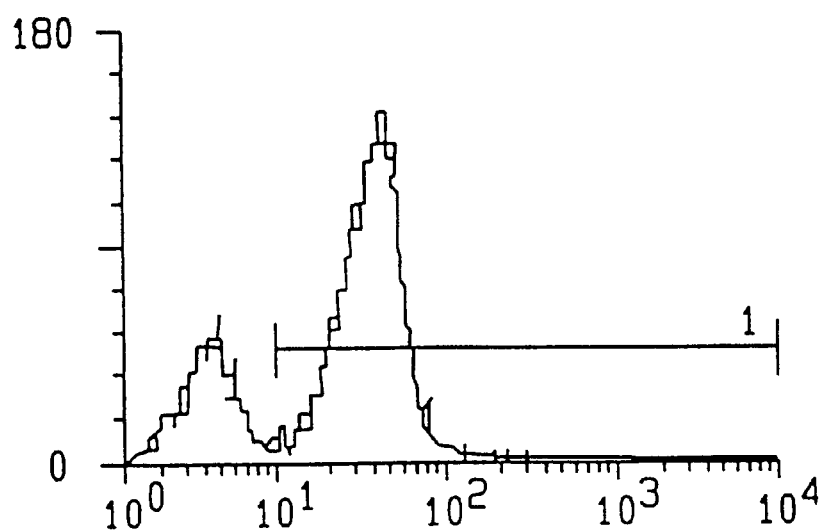

FIGS. 3A and 3B Anti-Thy1.2-treated donor bone marrow cells produce mixed allogeneic chimeras. Both syngeneic and allogeneic cells are detected.

5. DETAILED DESCRIPTION OF THE INVENTION

The present invention relates to MAb to antigens expressed by murine FC, methods of generating such antibodies and uses of such MAb. Although the specific procedures and methods described herein are exemplified using murine brain tissue for inducing rat MAb against mouse FC, they are merely illustrative for the practice of the invention. Analogous procedures and techniques are equally applicable to a variety of animal hosts immunized against brain tissue, partially purified FC or FC antigens for producing MAb against FC markers, including that expressed by human FC.

5.1. PREPARATION OF IMMUNOGENS

In order to generate MAb to antigens selectively expressed by FC, there are two major hindrances that must first be overcome. The first relates to the low quantities of FC in natural tissues and thus they need to be enriched to sufficient quantities and in relatively pure form for use as immunogens. It is estimated that it would require 4000 hours of cell sorting to obtain sufficient numbers of purified FC from bone marrow for use in immunization of one animal, if FC are purified to >95% purity.

Although the activity of FC allows for the use of these cells in relatively small numbers when enriched, it is preferred that they be enriched to >50% for use as immunogens. FC may be isolated from any tissues where they reside, using a variety of separation methods. In accordance with this aspect of the invention, human FC may be isolated from bone marrow. Procedures involving repetitive density gradient centrifugation, positive selection, negative selection, or a combination thereof may be used. For example, the human FC may be prepared by subjecting bone marrow aspirates to "FICOLL HYPAQUE" centrifugation. Positive selection does not necessarily require the use of antibodies that recognize FC-specific determinants. For example, B cells and monocytes may be depleted first from the FC-containing fraction after density gradient centrifugation, plastic adhesion, and Fc receptor panning, then an antibody to MHC-Class II antigen can be used to positively select for FC. Negative selection includes modifications of the protocol disclosed herein. For example, a FC-containing cell preparation may be reacted with one or more antibodies directed at cell surface antigens not expressed by FC for the removal of non-FC. Antibodies to a number of T cell, B cell, monocyte, and granulocyte markers may be used. Examples of such antibodies include anti-CD4 and anti-TCR specific for T cells; anti-CD12, anti-CD19 and anti-CD20 specific for B cells; anti-CD14 specific for monocytes; and anti-CD16 and anti-CD56 specific for natural killer cells. These antibodies may be applied in any combination repeatedly or in a sequential manner for the enrichment of FC. Upon binding to the antibodies, the cells may be removed by adsorption to a solid surface coated with an anti-mouse antibody, as the majority of monoclonal antibodies directed at human cell surface markers are of mouse origin, or if the antibodies are conjugated with biotin, the antibody-bound cells can be removed by an avidin or streptavidin-coated surface; or if the antibodies are conjugated to magnetic beads, the cells expressing antigens recognized by the antibodies can be removed in a magnetic field (Harlow and Lane, 1988, *Antibody: A Laboratory Manual,* Cold Spring Harbor).

Current methods for FC enrichment require a series of positive and negative selection steps, therefore other sources of FC-associated antigens may be used. For example, brain tissue appears to contain the same or cross-reactive antigens as that expressed by FC, and may be prepared for use as immunogens for the production of anti-human FC MAb. Brain tissue from any species may be obtained and prepared for use in immunization in the same manner as described in Section 6.1.2, infra, except that large tissue should be cut into small sections prior to homogenization.

The second hindrance relates to an efficient method for differential screening of the specific antibodies desired, i.e., to select for antibodies that are directed to FC but less so to other blood cells. For the purpose of the instant application, FC are defined as bone marrow-derived cells of about 8–10 microns in diameter, capable of enhancing stem cell engraftment, and which express Thy-1, CD3, CD8, CD45, CD45R, MHC class II (low to intermediate levels), but lack other markers such as CD4, CD5, CD14, CD16, CD19, CD20, CD56, $\gamma\delta$-TCR and $\alpha\beta$-TCR. MAb may be screened by binding assays in which the antibodies bind to FC but not or to a lesser degree to other bone marrow cells including stem cells, T cells, B cells, macrophages, monocytes, granulocytes, red blood cells and platelets. Antibody staining may be determined by flow cytometry or any other detection methods known in the art. Alternatively, antibodies may be screened for their ability to deplete FC function such as in an in vivo engraftment assay described in Section 6, infra.

5.2. ANTIBODY PRODUCTION

Various methods may be used to produce polyclonal and monoclonal antibodies that recognize novel antigenic markers expressed by FC. Any procedure known in the art may be used for the production of antibodies to these cells. For the production of antibodies, various host animals can be immunized by injection with viable, purified or partially purified FC or brain tissue, fixed cells or membrane preparations, including, but not limited to, those of rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

MAb which are substantially homogeneous antibodies to single antigenic epitopes on FC may be prepared by using any technique which provides for the production of antibody molecules by continuous cell lines in culture. These include, but are not limited to, the hybridoma technique originally described by Kohler and Milstein (1975, *Nature* 256, 495–497), the more recent human B-cell hybridoma technique (Kosbor et al., 1983, *Immunology Today* 4:72; Cote et al., 1983, *Proc. Natl. Acad. Sci.* USA 80:2026–2030) and the EBV-hybridoma technique (Cole et al., 1985, *Monoclonal Antibodies and Cancer Therapy. Alan R. Liss, Inc.,* pp. 77–96). MAb can be screened differentially by selective binding to FC, but not to mature macrophages, granulocyte, monocytes, T cells, B cells, stem cells and dendritic cells, and/or by inhibition of FC activity.

Antibody fragments which contain the binding site of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

A chimeric antibody is a molecule in which different portions are derived from different animal species, such as those having a variable region derived from a murine or rat MAb and a human immunoglobulin constant region. Techniques developed for the production of "chimeric antibodies" (Morrison et al., 1984, *Proc. Natl. Acad. Sci. USA* 81:6851; Neuberger et al., 1984, *Nature,* 312:604–608; Takeda et al., 1985, *Nature,* 314:452–454) by splicing the genes from a mouse antibody molecule of appropriate antigen specificity together with genes from a human antibody molecule of appropriate biological activity can be used. This approach is particularly useful if the antibodies are administered into humans. Chimeric antibodies present less xenogeneic epitopes in inducing an anti-rodent Ig response when injected in man.

Alternatively, techniques described for the production of single chain antibodies (U.S. Pat. No. 4,946,778; Bird, 1988, *Science* 242:423–425; Huston et al., 1988, *Proc. Natl. Acad. Sci. USA* 85:5879–5883; and Ward et al., 1989, *Nature* 334:544–546) can be adapted to produce FC-reactive single chain antibodies. Single chain antibodies are formed by linking the heavy and light chain fragment of the Fv region via an amino acid bridge, resulting in a single chain polypeptide.

Additionally, the whole antibody molecule or its Fab, $F(ab')_2$ or $F_v$ fragment may be conjugated to any of a variety of compounds including, but not limited to, signal generating compounds such as a fluorochrome, radio-isotope, a chromophore, an enzyme, a chemiluminescent or bioluminescent molecule, etc. Alternatively, the whole antibody or its Fab, F(ab')$_2$ or F$_v$ fragment may be conjugated to a cytokine which may enhance or inhibit the biological activity of FC; or to toxins so that FC which express the corresponding antigens would be selectively killed (Vitetta and Uhr, 1985, *Annu Rev. Immunol.* 3:197). Methods which can be used for conjugating labels, proteins, toxins etc. to antibodies and antibody fragments are well known in the art (See, for example, U.S. Pat. Nos. 4,220,450; 2,235,869; 3,935,074 and 3,996,345).

5.3. USES OF MONOCLONAL ANTIBODIES TO HEMATOPOIETIC FACILITATORY CELLS

A variety of uses of MAb are encompassed by the present invention. An antibody exhibiting exquisite specificity for FC in that it does not bind to T cells, B cells, NK cells, granulocytes, macrophages, monocytes, red blood cells, platelet and stem cells, may be used to isolate FC in a one step affinity cell separation procedure. Antibodies to markers that are selectively expressed by FC, i.e., certain but not all blood cells also express it, may still be used effectively in combination with other methods such as density gradient centrifugation to substantially reduce the time-consuming and cumbersome procedures currently employed for the isolation of FC.

For the practice of this aspect of the invention, a MAb may be conjugated to fluorochromes and used to select for FC from a cell mixture by flow cytometry using a fluorescence activated cell sorter or may be conjugated to biotin for use in biotin-avidin or biotin-streptavidin separations. In the latter method, avidin or streptavidin is bound to a solid support such as affinity column matrix or plastic surfaces. In addition, antibodies may be coated with magnetic beads, reacted with a cell mixture, and the antibody-bound FC removed by a magnetic field. Furthermore, such MAb may be conjugated to an enzyme for use in immunohistochemistry. For example, certain disorders may be induced or sustained by an aberrant function of FC, and detection of the level of FC in tissue sections may be of diagnostic value.

Additionally, MAb directed to FC markers may be used to isolate and identify the genes encoding such molecules. Antibodies may be used for screening expression libraries made from FC for the molecular cloning of the coding sequences (Seed and Aruffo, 1987, *Proc. Natl. Acad. Sci. USA* 84:3365–3369).

6. EXAMPLE

GENERATION OF MONOCLONAL ANTIBODIES TO MURINE HEMATOPOIETIC FACILITATORY CELLS

6.1. MATERIALS AND METHODS

6.1.1. ANIMALS

Six to eight week old male C57BL/10SnJ (B10), and B10.BR/SgSn (B10.BR) mice were purchased from the Jackson Laboratory (Bar Harbor, Me.). Four to eight week old male Fischer 344 (F344) male rats were purchased from Harlan Sprague Dawley, Inc. (Indianapolis, Ind.). Animals were housed in a specific pathogen-free facility at the Biomedical Science Tower at the University of Pittsburgh.

6.1.2. IMMUNIZATION AND CELL FUSION

Mouse brain tissue was obtained enbloc from calvarium. Brain tissue was placed in 1 ml PBS for each 1 cm$^3$ of brain tissue, which was homogenized in a glass homogenizer. Brain emulsion was then mixed with Complete Freund's Adjuvant at 1:1 ratio prior to animal injection. 0.4 ml of homogenized mouse brain was emulsified in adjuvant. Rat injections were done subcutaneously every 2 weeks for a total of four injections. Three days following the fourth injection, the peripheral blood was tested for antibody production. The animals exhibiting the strongest activities were then selected to be utilized for hybridoma fusion. The selected animals were then given an additional injection of brain/PBS mixture subcutaneously in the absence of complete Freund's adjuvant. This injection was generally about 5 to 6 days after the fourth injection. Two days following this fifth injection, the spleens of the animals were harvested and fused with HGPRT$^-$myeloma cells (P3.653) using polyethylene glycol (Kohler and Milstein, 1975, *Nature* 256:495). The cells were then distributed in microwell plates and grown in HAT medium (RPMI-1640 supplemented with 10% fetal bovine serum, 1% Pen/Strep, 1% L-glutamine, 1% non-essential amino acids, 1% sodium pyruvate and HAT). The unfused myeloma cells died because of their lack of HGPRT$^-$to use the salvage pathway. The unfused spleen cells also died because they were unable to grow in vitro. The fused cells (hybridomas) grew in the microwells and their culture supernatants were first tested for the production of rat antibodies.

The culture supernatant was screened for the presence of rat anti-mouse antibodies by incubating $10^6$ mouse bone marrow cells in small flow tubes with rat serum to block non-specific rat antibody staining. 20–30 $\mu$l of hybridoma culture supernatant was then added to each tube of bone marrow, two separate tubes were tested for each supernatant—one to screen for IgG production and the other for IgM production. Following a 45 min. incubation at 4° C., cells were washed twice at 1000 rpm×10 min. and the media decanted. Pre-titered goat-anti-rat IgG-FITC was added to the first tube for each culture supernatant, and anti-rat IgM-PE was added to the second tube. After 45 minute incubation at 4° C., the cells were washed twice and fixed in 0.4 ml of 1% paraformaldehyde for subsequent flow cytometric analysis. The controls included samples with cells alone, IgG alone, IgM alone as assessments of background staining and negative controls; and RAMB, Lyt2-FITC, and unlabelled rat IgG and IgM MAb against known mouse antigens as positive controls. Hybridomas were selected for the production of rat anti-mouse antibodies which cross reacted with distinct populations of mouse bone marrow. The positive wells were further screened for antibodies directed to FC in an in vivo assay. The selected hybridomas were cloned by limiting dilution. The cloned hybridomas were injected into pristane-primed nude mice for the production of ascites.

6.1.3. PREPARATION OF MIXED ALLOGENEIC CHIMERAS

In order to screen and select for MAb directed to FC, a preparation of donor bone marrow cells was reacted with hybridoma supernatants prior to their injection into allogeneic mouse recipients. Mixed allogeneic chimerism in the recipients was used as an indicator of the presence of MAb capable of depleting FC function. To prepare mixed chimeras, bone marrow from the long bones of syngeneic (B10) mice and allogeneic (B10.BR) mice were harvested. The mice were euthanized with $CO_2$ narcosis, prepared with 70% alcohol, and the long hind bone (femora and tibia) removed. The marrow was flushed from the bones using medium 199 (Gibco Laboratories Life Technology, Inc., Grand Island, N.Y.) supplemented with 50 $\mu$l/ml of gentamicin using a 22-gauge needle. The medium mixture (MEM) was used to mechanically resuspend the bone marrow by gentle aspiration through an 18-gauge needle and the suspension filtered through sterile nylon mesh gauze. The cells were then pelleted at 1000 rpm for 10 minutes, resuspended in MEM, and counted. In standard allogeneic reconstitution, RAMB was used for T-cell depletion of syngeneic B10 bone marrow (1:40 or appropriate dilution at $10^8$ cells/ml at 4° C. for 30 minutes). RAMB was prepared in the same manner as that described for immunization of rats with mouse brain in Section 6.1.2, supra, except that mouse brain was used to immunize rabbits. The allogeneic B10.BR bone marrow cells were either untreated, RAMB-depleted, anti-Thy1.2 depleted or hybridoma supernatant treated. $10 \times 10^6$ donor bone marrow cells were pelleted and antibodies added 1:10 in 1 ml. The media were prewarmed to 37° C. so that the antibody incubation was performed at 37° C. for 30 minutes. Cells were then washed in MEM, spun at 1000 rpm for 10 minutes and resuspended in guinea pig complement at 37° C. for 30 minutes (Gibco Laboratories Life Technology, Inc., Grand Island, N.Y.). Cells were washed twice, counted and resuspended in MEM at the appropriate concentration to allow injection of 1 ml of total volume per animal. The RAMB-treated syngeneic cells were injected at $5 \times 10^6$/animal, whereas the allogeneic cells were given at $15 \times 10^6$/animal within 4–6 hours after irradiation of recipient animals at 9.5 Gy. Cell injections were via the lateral tail veins using a 27-gauge needle.

6.1.4. CHARACTERIZATION OF CHIMERAS BY FLOW CYTOMETRY

Recipients were characterized for engraftment with syngeneic and allogeneic donor lymphoid elements using flow cytometry to determine the percentage of peripheral blood leukocytes (PBL) bearing MHC Class I ($H-2^b$ or $H-2^k$) surface markers. Briefly, peripheral blood was collected into heparinized plastic serum vials. After thorough mixing, the suspension was layered over 1.5 ml of room temperature lymphocyte separation medium (LSM) (Organon Technical, Kensington, Md.) and centrifuged at 20° C. at 1700 rpm for 30 minutes. The lymphocyte layer was aspirated from the saline-LSM interface and washed with medium. Red blood cells were ACK-lysed (ammonium chloride/potassium carbonate lysing buffer) and the remaining cells stained with appropriate MAb for 30 minutes at 4° C. and counterstained with sandwich when required. Analyses of splenic and thymic lymphoid cells were performed using a fluorescence activated cell sorter (FACS) (FACS II Becton Dickinson and Company, Mountain View, Calif.).

6.2. RESULTS

The experiments described in the following sections utilized a mixed chimera model in which recipient animals were lethally-irradiated and transplanted with fixed doses of allogeneic donor cells and syngeneic donor cells. The percentage of allogeneic chimerism, i.e., the level of mixed chimerism was used as a read-out of FC activity in promoting donor cell engraftment.

It was previously reported that RAMB and complement treatment of a bone marrow preparation negatively affected its ability to engraft in a recipient. Recently, a bone marrow cell population referred to as FC has been identified, which greatly enhanced hematopoietic stem cell engraftment. In allogeneic bone marrow transplantation, $Sca-1^+$purified hematopoietic stem cells alone were not able to engraft unless FC were co-administered. Furthermore, FC did not possess stem cell activity. Since RAMB appeared to deplete FC and RAMB was an antiserum raised against mouse brain, it was possible that mouse FC shared certain common or cross-reactive antigens with mouse brain tissues. Thus, mouse brain tissues were obtained, homogenized and used as immunogens in rats for the production of MAb against markers expressed by mouse FC.

After several immunizations with mouse brain tissues, rats were sacrificed and their spleen cells fused with $HGPRT^-$myeloma cells by polyethylene glycol. The resulting hybridoma cells were selected in HAT medium and their culture supernatants tested for their ability to reduce the level of donor bone marrow engraftment in allogeneic recipients as an indication of the presence of antibodies capable of eliminating FC.

The antibody screening procedure utilized an established mixed allogeneic chimerism model in which mouse recipients received TCD-syngeneic bone marrow cells plus allogeneic bone marrow cells treated with various antibodies. The level of allogeneic chimerism in the recipients was determined by the use of anti-MHC class I antibodies, and it was used as a an indication of the effects of antibodies on FC function. For example, an untreated allogeneic donor bone marrow preparation led to fully allogeneic recipients, i.e. primarily $H-2^k$ allogeneic cells, with few syngeneic ($H-2^b$) cells were detected in the recipients (FIGS. 1A and 1B). On the other hand, allogeneic donor cells treated with RAMB (FIGS. 2A and 2B) or anti-Thy1.2 (FIGS. 3A and 3B) antibody led to mixed allogeneic chimerism, indicating that these reagents depleted FC which were needed to promote allogeneic stem cell engraftment.

As compared to these controls, donor bone marrow cells were treated with hybridoma supernatants and subsequently transplanted into allogeneic recipients to select for antibodies that would produce mixed allogeneic chimerism similar to the results obtained with RAMB or anti-Thy1.2 treatment. Antibodies that did not reduce the level of full allogeneic chimerism were discarded since they were not able to remove FC.

Out of the numerous hybridomas generated and the ones tested in the aforementioned assay, three hybridoma cell lines designated R7.6.2 (IgG2a), R340.3.1 (IgM) and R373.6.3 (IgM) were selected for further studies. These cell lines produced antibodies which were directed to FC markers as evidenced by their ability to cause mixed allogeneic chimerism in recipients transplanted with donor cells treated with them, while untreated donor cells produced fully allogeneic chimeras (Table I). These results indicated that the three MAb were directed to FC, capable of depleting FC in the donor cell preparation and in turn, causing a diminution in the ability of the stem cells to engraft. Out of a total of greater than 150 hybridomas screened, only three clones produced antibodies that bound preferentially to FC.

TABLE 1

| MONOCLONAL ANTIBODIES DIRECTED TO FC | | | |
| --- | --- | --- | --- |
| CLONE | # animal | $H-2^b$ (syngeneic) | $H-2^k$ (allogeneic) |
| R7.6.2 | #959 | 18.90 | 79.12 |
|  | #961 | 12.12 | 86.98 |
|  | #962 | 12.48 | 91.18 |
|  | #964 | 10.66 | 93.26 |
|  | #966 | 27.35 | 70.34 |
|  | #967 | 12.58 | 88.18 |
| R340.3.1 | #965 | 40.06 | 67.98 |

TABLE 1-continued

MONOCLONAL ANTIBODIES DIRECTED TO FC

| CLONE | # animal | H-2$^b$ (syngeneic) | H-2$^k$ (allogeneic) |
|---|---|---|---|
| | #968 | 9.2 | 98.24 |
| R373.6.3 | #773 | 85.54 | 13.91 |
| | #774 | 97.28 | 0.54 |
| | #775 | 35.89 | 57.57 |
| | #974 | 99.76 | 0.38 |
| RAMB | #272 | 50.78 | 48.02 |
| Depletion | #273 | 49.22 | 46.72 |
| | #274 | 49.34 | 44.04 |
| | 275 | 97.54 | 5.74 |
| Anti-Thy1.2 | #969 | 63.34 | 33.56 |
| Depletion | #971 | 64.52 | 32.90 |
| B10 Control | | 92.52 | 0.56 |
| B10BR Control | | 0.96 | 99.24 |

7. DEPOSIT OF CELL LINE

The following hybridoma cell lines were deposited with the American Type Culture Collection 10801 University Boulevard, Manassas, Va. 20110-2209 on Jan. 4, 1994, Jan. 4, 1994, and Dec. 10, 1993, respectively, and assigned the following accession numbers:

| Hybridoma | ATCC Accession Number |
|---|---|
| T7.6.2 | HB11517 |
| R340.3.1 | HB11518 |
| R373.6.3 | HB11507 |

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. Monoclonal antibody produced by hybridoma R.7.6.2. as deposited with the American Type Culture Collection under accession no. HB11517.

2. Monoclonal antibody produced by hybridoma R340.3.1. as deposited with the American Type Culture Collection under accession no. HB11518.

3. Monoclonal antibody produced by hybridoma R373.6.3 as deposited with the American Type Culture Collection under accession no. HB11507.

4. Hybridoma R.7.6.2. as deposited with the American Type Culture Collection under accession no. HB11517.

5. Hybridoma R340.3.1. as deposited with the American Type Culture Collection under accession no. HB11518.

6. Hybridoma R373.6.3 as deposited with the American Type Culture Collection under accession no. HB11507.

* * * * *